(12) United States Patent
Refaei et al.

(10) Patent No.: US 8,187,468 B2
(45) Date of Patent: May 29, 2012

(54) PREPARATION AND USE OF CHIRAL ZEOLITES FOR LIQUID CHROMATOGRAPHY

(75) Inventors: Mohd Refaei, El Paso, TX (US); James Salvador, El Paso, TX (US)

(73) Assignee: University of Texas at El Paso, El Paso, TX (US)

( * ) Notice: Subject to any disclaimer, the term of this patent is extended or adjusted under 35 U.S.C. 154(b) by 416 days.

(21) Appl. No.: 12/556,204

(22) Filed: Sep. 9, 2009

(65) Prior Publication Data

US 2010/0089831 A1    Apr. 15, 2010

Related U.S. Application Data

(60) Provisional application No. 61/097,810, filed on Sep. 17, 2008.

(51) Int. Cl.
*B01D 15/08*    (2006.01)

(52) U.S. Cl. ............... 210/656; 210/635; 210/198.2; 210/502.1; 502/400; 502/439; 423/706

(58) Field of Classification Search ............... 210/635, 210/656, 659, 198.2, 502.1; 502/401, 439; 423/706; 428/405
See application file for complete search history.

(56) References Cited

U.S. PATENT DOCUMENTS

| | | | |
|---|---|---|---|
| 5,756,789 A * | 5/1998 | Bruce et al. | 556/14 |
| 7,906,096 B2 * | 3/2011 | Bae et al. | 423/447.2 |
| 8,063,114 B2 * | 11/2011 | Tatsumi et al. | 521/154 |
| 2002/0013475 A1 * | 1/2002 | MacMillan et al. | 548/311.1 |
| 2009/0018334 A1 * | 1/2009 | Bae et al. | 544/225 |
| 2010/0089831 A1 * | 4/2010 | Refaei et al. | 210/656 |

* cited by examiner

*Primary Examiner* — Ernest G Therkorn
(74) *Attorney, Agent, or Firm* — Fulright & Jaworski L.L.P.

(57) ABSTRACT

The present invention relates to the preparation of chiral zeolites and their use in liquid chromatography. The zeolite material may be used in the chromatographic separation of mixtures of components, such as the separation of enantiomers.

13 Claims, 8 Drawing Sheets

A

B

A

B

A

B

A

B

A

B

PREPARATION AND USE OF CHIRAL ZEOLITES FOR LIQUID CHROMATOGRAPHY

This application claims the benefit of U.S. Provisional Application Ser. No. 61/097,810, filed Sep. 17, 2008, the entire contents of which are hereby incorporated herein by reference.

BACKGROUND OF THE INVENTION

I. Field of the Invention

The present invention relates generally to the liquid chromatographic separation of components in a mixture. More particularly, the invention pertains to chiral zeolites as stationary phase for liquid chromatography columns, the preparation of this material, and methods of separating components, such as enantiomers, using this material.

II. Related Art

A molecule is chiral if it cannot be superimposed upon its mirror image and would exhibit optical activity. Enantiomers are examples of chiral compounds which have the same molecular formula and connectivity, but different orientation in three dimensional space. Their orientation in space is in such a way that they are the minor images of one another. A simple example would be right and left handed gloves. Such characteristics often influence their chemical interaction with the surrounding environment and may provide each with different types of interactions with proteins or other agents (Neue, 1997).

This differential behavior of enantiomers often becomes crucial in the synthesis and purification of pharmaceutical agents. A typical goal of pharmaceutical companies is to either make an agonist or antagonist for a cell surface receptor. For example, in the case of familial hypercholesterolemia disease, either the cholesterol receptors are defective in their structures or they are not synthesized at a normal rate. Both types of deficiencies result from an underlying genetic defect. The medication Lipitor® (atorvastatin), an R enantiomer, inhibits the enzyme that synthesizes cholesterol in the liver, causing a 25-45% drop in the serum cholesterol level. Side effects of such medication are usually nausea, vomiting, liver necrosis, muscle degeneration and fatigue. The main cause of such adverse effects is the presence of the S enantiomer, synthesized during manufacturing. The undesired enantiomer interacts differently at sites other than the cholesterol receptor site. Separation of the R and S enantiomers, therefore, is beneficial.

Pharmaceutical companies also use chirality as a tool to extend their patent lives of their blockbuster drugs. One example is the commercialization of the drug Nexium® by AstraZeneca. Nexium® is the S enantiomer of a racemic mixture previously sold as Prilosec®. The patent for Prilosec® expired in 2002 at which time the company then marketed the S enantiomer, Nexium®, to generate another decade of a blockbuster anti-ulcer drug sales (Stinson, 2007).

Another example of the importance of chirality lies in the purity analyses required by governmental agencies with respect to the manufacture and selling of pharmaceuticals. Regulatory authorities require thorough documentation regarding a drug substance, including chiral purity and stability. These requirements create a growing demand for rapid, precise and sensitive methods for analysis of enantiomeric purity (Peterson, 1997).

Liquid chromatography is a method commonly used to separate and purify components such as organic molecules and proteins. In this method, a stationary phase is subjected to mobile liquid phase in which a mixture of compounds is dissolved. In liquid chromatography that employs a column, the stationary phase is packed into the column and the liquid phase that carries the mixture to be analyzed passes through the column. Various properties of the components of the mixture, as well as the chosen stationary and mobile phases, may be exploited in order to best separate the components, such that the separate components elute from the column at different times. Unfortunately, enantiomers are often not easily separable by techniques that can separate other isomers or components due to their similar chemical structures.

There has never been a single liquid chromatography column capable of separating all enantiomeric mixtures. Thus, there is a perpetual demand for the development of new liquid chromatography columns for separation as more molecules are synthesized whose enantiomers exhibit different physiological characteristics.

SUMMARY OF THE INVENTION

The present invention involves the preparation and use of chiral zeolites. These zeolites may be used as the stationary phase in liquid chromatography for the chromatographic separation of components of a liquid sample. Such components may be enantiomers. The chiral zeolites of the present invention, which may be prepared in an inexpensive and relatively simple procedure, may be packed into liquid chromatography columns of any size or type (e.g., analytical, preparatory, normal phase, reversed-phase, high performance liquid chromatography (HPLC) columns, etc.).

In general, chiral zeolites are prepared by a method that comprises refluxing a mixture comprising a chiral organic compound, sodium silicate, and $Al^{3+}$ such that a crystalline zeolite structure is formed that incorporates the chiral organic compound. The zeolite is then calcinated such that the chiral organic compound is degraded or evaporates, leaving behind chiral pores in the zeolite. As discussed herein, if the chiral organic compound is a cation, additional cationic species (e.g., alkali metal ions) are typically not needed to be added to the mixture to be refluxed. If the chiral organic compound is not a cation, such cationic species may need to be added to promote crystalline zeolite formation.

In certain embodiments, following the preparation of a first chiral zeolite using a first chiral organic compound, an enantiomer of that chiral organic compound may be used to generate a second chiral zeolite. A liquid sample comprising two or more components may be separately subjected to each type of zeolite material as comprised in separate columns such that the components elute from each column in a different (e.g., opposite) order or with varying degrees of separation (e.g., peak overlap). This may allow for better analysis or separation of those components. This option of preparing a "mirror image" column is often not possible in other types of chromatography.

Furthermore, a variety of components may be subjected to the chiral zeolites for chromatographic separation, including organic compounds (including polymers), peptides and proteins. For example, organic compounds having a particular molecular weight, as described above in the definition of organic compounds, may be separated using the materials and methods described herein, in certain embodiments. The components may be charged or uncharged. Thus, for example, uncharged organic molecules having a molecular weight of 100-1000 g/mol may be separated, in certain embodiments. The components may be chiral or achiral. For example, separation of two enantiomers may be performed, such as enantiomers that are organic molecules having a molecular weight of 100-1000 g/mol. Peptides of 1-10 amino acids in length, for example, may be separated. A variety of drugs may be separated, such as non-steroidal anti-inflammatory (NSAID) drugs may be separated, in certain embodiments. In certain embodiments, organic compounds comprising an alcohol substituent may be separated from other components in a mixture. In certain embodiments, components exhibiting a particular hydrophobicity may be separated. Methods of measuring hydrophobicity are well-known in the art, including methods based on a component's water/octanol partition coefficient. Thus, for example, compounds exhibiting a water/octanol partition coefficient within two water/octanol partition coefficient values (log P) of trans-2-(N-methyl-N-phenylamino)cyclohexanol (MPAC), trans-2-(1-methyl-1-phenylethyl)cyclohexanol (TCC), or ibuprofen may be employed. Combinations of any of these or other chemical classes or properties known to those of skill in the art may characterize types of components that may be separated using the materials and methods discussed herein.

The pores of the zeolites, which are typically much larger than the size of individual components, may interact with components in a manner that differs from the stationary phases used in other types of chromatography, such as size-exclusion chromatography or ion-exchange chromatography, thus allowing for better chromatographic separation of the components.

Chiral zeolite liquid chromatography columns as described herein may be employed using a wide range of pH and pressure values. For example, a pH range of about 5-10 and pressure ranges up to those typically employed in HPLC (e.g., up to 1000 psi) may be used with the chiral zeolites described herein.

Accordingly, the present invention generally relates to a packing material for liquid chromatography comprising zeolites, wherein the zeolites comprise a plurality of chiral pores. Herein, zeolites that comprise a plurality of chiral pores are termed "chiral zeolites." The chiral pores may be formed, for example, by evaporation or degradation of a chiral organic compound, as defined herein. In certain embodiments, a chiral organic compound may have a molecular weight of about 200-700 g/mol. In certain embodiments, the chiral organic compound is further defined as a compound of formula (I):

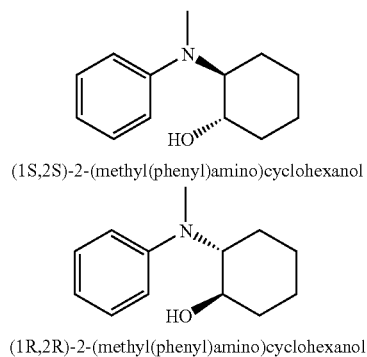

wherein: A, B, D, E and G are each independently carbon or nitrogen; $R_1$-$R_5$ are each independently absent, hydrogen, or alkyl$_{(C \leq 4)}$, wherein if any of A, B, D, E, or G is nitrogen, then $R_1$-$R_5$ is absent; $R_6$ is alkyl$_{(C \leq 4)}$; $R_7$-$R_{10}$ are each independently hydrogen, or alkyl$_{(C \leq 4)}$; the bonds marked "a" and "b" are cis or trans to one another; and n=0 or 1, such that when n=0, then the ring marked as "B" is a five-membered ring, and when n=1, the ring marked as "B" is a six-membered ring. Compounds of formula (I) may be prepared synthetically, as described herein, or purchased from commercial sources. In certain embodiments, at least four of $R_1$-$R_4$ and $R_6$-$R_9$ are hydrogen. In certain embodiments, each of $R_1$-$R_5$ and $R_6$-$R_9$ is hydrogen. In certain embodiments, $R_6$ is methyl. In certain embodiments, one or two of A, B, D, E and G are nitrogen. In other embodiments, each of A, B, D, E and G are carbon. In certain embodiments, the "a" and "b" bonds are cis, whereas in other embodiments, the "a" and "b" bonds are trans. In particular embodiments, n=1. In certain embodiments, n=0.

In certain embodiments regarding compounds of formula (I), the compound of formula (I) may be further defined as trans-2-(N-methyl-N-phenylamino)cyclohexanol or cis-2-(N-methyl-N-phenylamino)cyclohexanol. In certain embodiments, trans-2-(N-methyl-N-phenylamino)cyclohexanol is further defined as 1S,2S-2-(N-methyl-N-phenylamino)cyclohexanol. In certain embodiments, trans-2-(N-methyl-N-phenylamino)cyclohexanol is further defined as 1R,2R-2-(N-methyl-N-phenylamino)cyclohexanol. These structures are shown below.

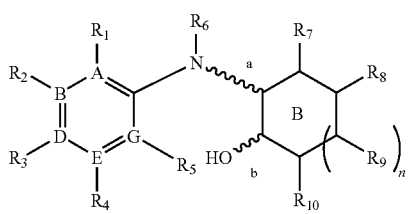

(1S,2S)-2-(methyl(phenyl)amino)cyclohexanol (1R,2R)-2-(methyl(phenyl)amino)cyclohexanol The packing material may been calcinated at temperatures ranging from about 525-575° C., for example. In certain embodiments of this or any other embodiment described herein, the temperature is about, at most about, or at least about 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, or 575° C., or any range derivable therein.

Non-limiting examples of liquid chromatography in this or any other embodiment herein include no-pressure liquid chromatography (wherein gravity is utilized), low-pressure liquid chromatography and high performance liquid chromatography (HPLC). These and other types of liquid chromatography are well-known in the art.

The present invention also contemplates a liquid chromatography column comprising a packing material that comprises zeolites, wherein the zeolites comprise a plurality of chiral pores. The liquid chromatography column may be, for example, a no-pressure, low-pressure, or HPLC column. In particular embodiments, the liquid chromatography column is an HPLC column. The HPLC column may be a normal phase HPLC column or a reversed-phase HPLC column, as those terms are known in the art. The chiral pores may be formed by any method described herein, such as by evaporation or degradation of a chiral organic compound, such as a chiral organic compound having a molecular weight of about 200-700 g/mol. The chiral organic compound may be a compound of formula (I), as that formula is described above.

Other general aspects of the present invention contemplate a method of making a packing material for liquid chromatography comprising: (a) forming a first mixture by combining sodium silicate and a compound of formula (I), as that formula is described above; (b) adding $Al^{3+}$ to the first mixture to form a second mixture; (c) refluxing the second mixture; and (d) calcinating the second mixture to form the packing material. The source of $Al^{3+}$ may be aluminum hydroxide, for example, or any other aluminum salt, such as aluminum acetate or aluminum chloride. Methods of the present invention may further comprise packing a liquid chromatography column with the packing material. Persons of skill in the art are familiar with methods of packing liquid chromatography columns. Methods may further comprise adding aminopropyltriethoxysilane (APTS) to either the first or second mixture before refluxing. In certain embodiments, the molar ratio of aminopropyltriethoxysilane to the compound of formula (I) is about 0.1:2 to 2:0.1. In certain embodiments, the ratio is about 0.75:1.25 to 1.25:0.75. In certain embodiments, the ratio is about 1:1. The molar ratio of sodium silicate to the compound of formula (I) may range from about 0.1:2 to 2:0.1, for example. In certain embodiments, the ratio is about 0.1:1 to 1:1. In certain embodiments, the range is about 0.3:1. The calcination temperature may be performed at a temperature ranging from about 525-575° C., or any temperature within this range, as described above.

In certain embodiments, methods may further comprise washing the second mixture with at least one organic solvent. The organic solvent may be a polar solvent, such as methanol, ethanol, isopropanol, or acetonitrile. The organic solvent may be a non-polar solvent, such as pentane, hexanes, or toluene. The second mixture may alternatively be washed with a polar solvent and then a non-polar solvent, or vice-versa.

Methods of separating components in a liquid mixture are also contemplated. Such methods may comprise liquid chromatographic separation of at least two components comprised in a liquid composition, comprising subjecting the liquid composition to the packing material described herein. By "separation," it is meant that a component of interest is separated from other components in a mixture such that the purity of the component of interest is improved compared to the purity of the component prior to the chromatographic separation. By "subjecting," it is meant that the liquid is placed into physical contact with the packing material. Typically, the components in the liquid mixture are dissolved in a liquid or combination of liquids prior to subjecting them to the packing material. In certain embodiments, at least two of the components are enantiomers. The packing material may be comprised in a liquid chromatography column, as described herein, such as a normal phase liquid chromatography column, a reversed-phase liquid chromatography column, or an HPLC column.

Also contemplated by the present invention is an isolated compound defined as 1S,2S-2-(N-methyl-N-phenylamino)cyclohexanol. By "isolated," it is meant that the compound is substantially free of other enantiomers. By "substantially free," it is meant that any other enantiomers are present in a total amount of less than 0.5%. In certain embodiments, any other enantiomers are present in a total amount of less than about 0.5%, 0.4%, 0.3%, 0.2%, 0.1%, or lower, or any range derivable therein.

A method of making isolated 1S,2S-2-(N-methyl-N-phenylamino)cyclohexanol is also contemplated by the present invention, comprising: (a) preparing a first mixture comprising 1S,2S-2-(N-methyl-N-phenylamino)cyclohexanol and 1R,2R-2-(N-methyl-N-phenylamino)cyclohexanol; (b) combining the first mixture with a $C_4$-$C_{50}$ fatty acid to form a second mixture that comprises an ester of 1R,2R-2-(N-methyl-N-phenylamino)cyclohexanol; and (c) reacting the second mixture with *Candida rugosa* lipase; and (d) isolating 1S,2S-2-(N-methyl-N-phenylamino)cyclohexanol. Isolation may be performed by, for example, chromatography, such as radial chromatography. The fatty acid may be a $C_4$-$C_{30}$ fatty acid, such as lauric acid. The method may further comprise monitoring the reaction of step (c) for the production of the ester of 1R,2R-2-(N-methyl-N-phenylamino)cyclohexanol. In certain embodiments, cyclohexane is combined with the components of step (a) and (b). Methods of preparing the racemic mixture of part (a) are well-known in the art. See, e.g., Swamy and Raghavendra, 2002, incorporated herein in its entirety.

As used herein, "zeolite" is a generic name for crystalline aluminosilicates and refers to a crystalline complex oxide where aluminum and silicon atoms are tetrahedrally coordinated.

In certain methods of the present invention, chiral organic compounds are combined with silica during preparation of silica gel, followed by calcination of the silica gel to form a packing material, which may be a chiral zeolite. As discussed herein, calcination removes the chiral organic compounds through the use of heat, such as by evaporation or degradation, such that pores are left behind in the packing material. As used herein, these pores are called "chiral pores."

Persons of skill in the art are familiar with the term "organic compounds." Organic compounds of the present invention include chiral organic compounds. In certain embodiments, organic compounds of the present invention are small organic molecules having a molecular weight of 750 g/mol or less. In certain embodiments, organic compounds are polymers. In certain embodiments, the organic compound has a molecular weight of less than 500,000 g/mol. In certain embodiments, the organic compound has a molecular weight of about, at least about, or at most about 500,000, 450,000, 400,000, 350,000, 300,000, 250,000, 200,000, 150,000, 100,000, 75,000, 50,000, 25,000, 10,000, 9000, 8000, 7000, 6000, 5000, 4000, 3000, 2000, 1000, 750, 500, 250, or 100 g/mol, or lower, or any range derivable therein. In certain embodiments, the organic compound has a molecular weight of higher than 500,000 g/mol. An organic compound may be a chiral organic compound, which is defined below.

The term "alkyl" refers to a non-aromatic monovalent group having a saturated carbon atom as the point of attachment, a linear or branched, cyclo, cyclic or acyclic structure, no carbon-carbon double or triple bonds, and no atoms other than carbon and hydrogen. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, cyclohexyl, and cyclohexylmethyl are non-limiting examples of alkyl groups.

For any embodiment that employs an alkyl group, such as described in the compound of formula (I) above, a substituted alkyl group may alternatively be employed. The term "substituted alkyl" refers to a non-aromatic monovalent group, having a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —$CH_2OH$, —$CH_2Cl$, —$CH_2Br$, —$CH_2SH$, —$CF_3$, —$CH_2CN$, —$CH_2C(O)H$, —$CH_2C(O)OH$, —$CH_2C(O)OCH_3$, —$CH_2C(O)NH_2$, —$CH_2C(O)NHCH_3$, —$CH_2C(O)CH_3$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, —$CH_2CF_3$, —$CH_2CH_2OC(O)CH_3$, —$CH_2CH_2NHCO_2C(CH_3)_3$, and —$CH_2Si(CH_3)_3$.

A "stereoisomer" or "optical isomer" is an isomer of a given compound in which the same atoms are bonded to the same other atoms, but where the configuration of those atoms in three dimensions differs. "Enantiomers," which are chiral, are stereoisomers of a given compound that are mirror images of each other, like left and right hands. "Diastereomers" are stereoisomers of a given compound that are not enantiomers. Chiral organic compounds comprise at least one chiral center, which is an $sp^3$ hybridized carbon atom that is bonded to four different substituents.

The terms "a" and "an" are defined as one or more unless this disclosure explicitly requires otherwise.

The use of the term "or" in the claims is used to mean "and/or" unless explicitly indicated to refer to alternatives only or the alternatives are mutually exclusive, although the disclosure supports a definition that refers to only alternatives and "and/or."

The term "about" refers to ranges within 10%, such as within 5%, within 1%, or within 0.5% of what is specified.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has," or "includes" one or more steps is not limited to possessing only those one or more steps and also covers other unlisted steps. Furthermore, a device or structure that is configured in a certain way is configured in at least that way, but may also be configured in ways that are not listed.

Other features and associated advantages will become apparent with reference to the following detailed description of specific embodiments.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

FIG. 2A: 350° C., where the 1S,2S MPAC enantiomer is still retained in the bulk of the gel. FIG. 2B: 400° C., showing some cracking and evaporation of the 1S,2S MPAC enantiomer from the sample. FIG. 3A: 450° C. showing little difference from the 400° C. sample. FIG. 3B: 500° C., where pores are barely forming. FIG. 4A: 550° C., showing formation of ordered pores. FIG. 4B: 550° C., showing a different view of ordered pores. FIG. 5A: 575° C., showing formation of fibers. FIG. 5B: 600° C., showing tube-like structures. FIG. 6: 650° C., with closure and fusion of the ordered pores observed at 550° C.

FIG. 8A: 1:0.25 sodium silicate: 1S,2S MPAC enantiomer. FIG. 8B: 1:2 sodium silicate:1S,2S MPAC enantiomer.

DETAILED DESCRIPTION OF THE INVENTION

Figure 1:
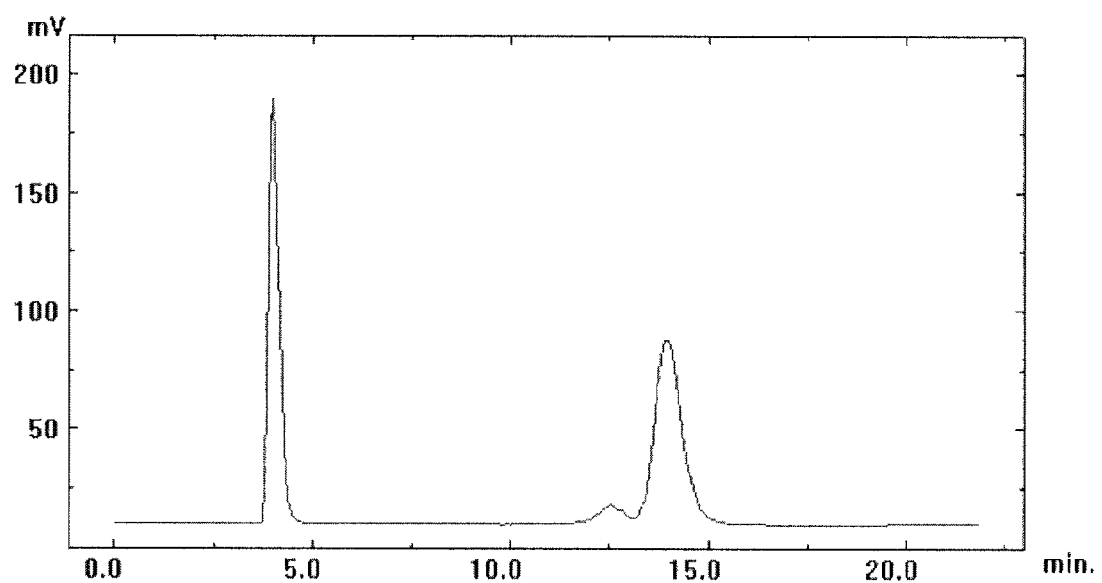
FIG. 1. HPLC chromatogram monitoring esterification reaction during racemic MPAC resolution. Chiralcel® OJ; 5% isopropanol, 95% hexanes; 1 mL/min.
Figure 2:
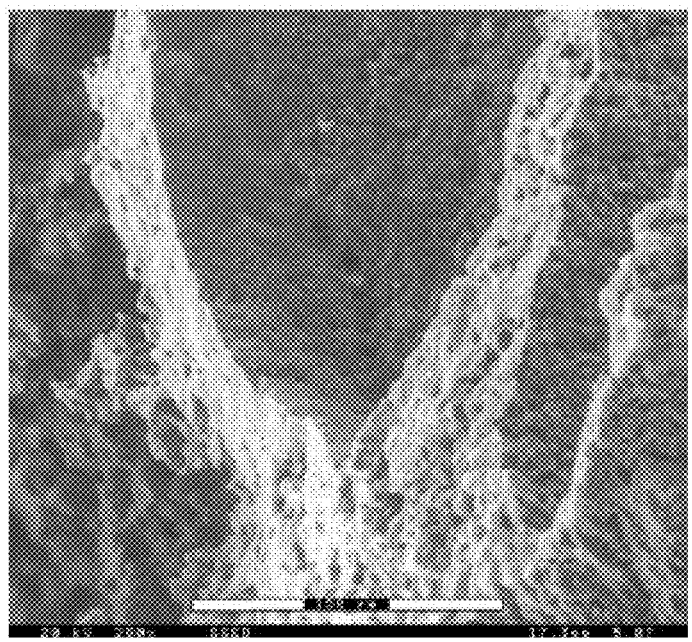
FIGS. 2-6. Scanning electron micrographs of chiral zeolites formed with the 1S,2S MPAC enantiomer calcined at various temperatures.
Figure 2:
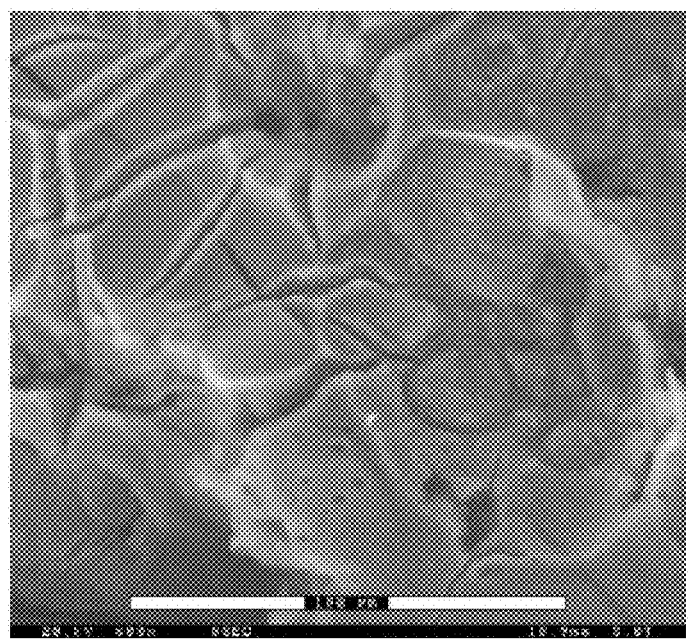
Figure 3:
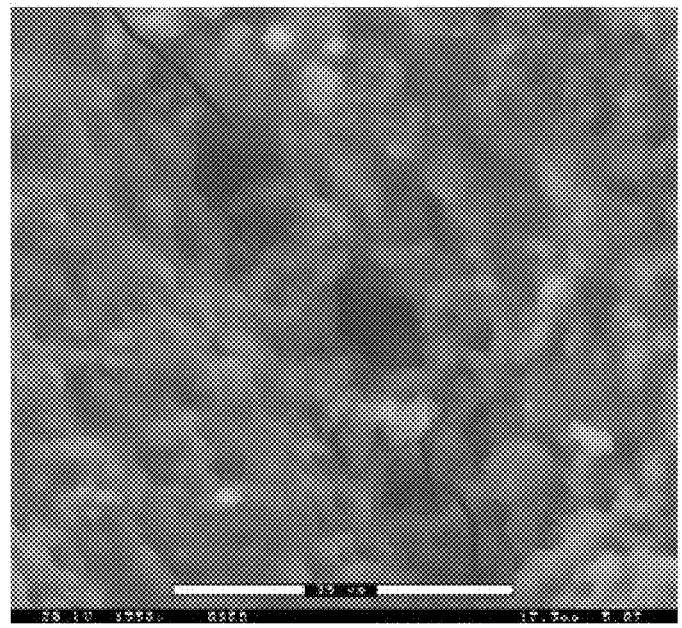
Figure 3:
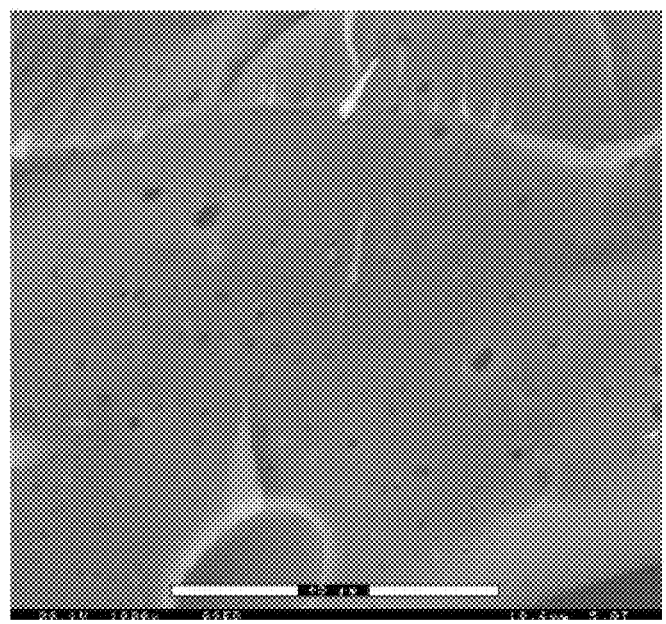
Figure 4:
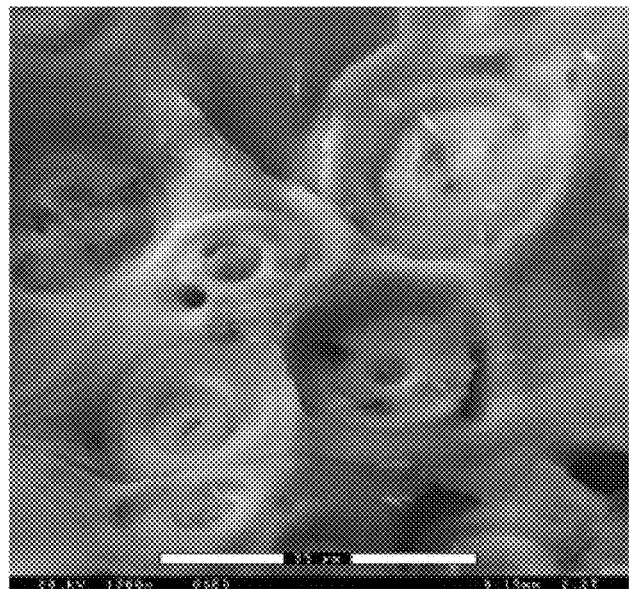
Figure 4:
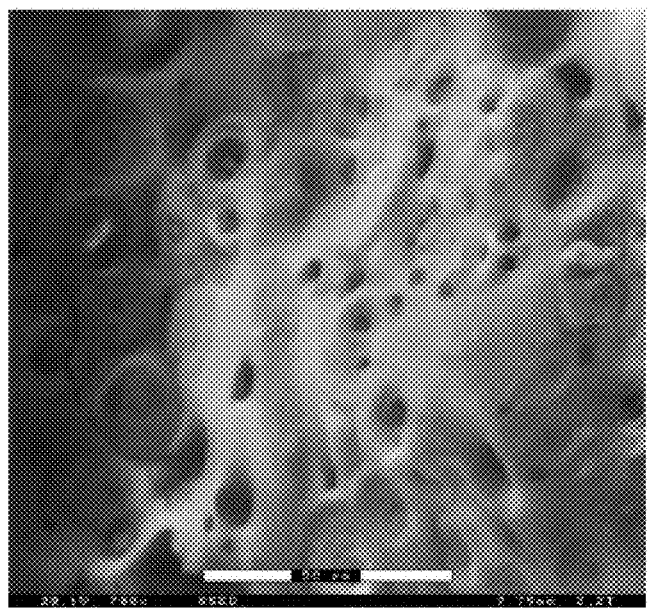
Figure 5:
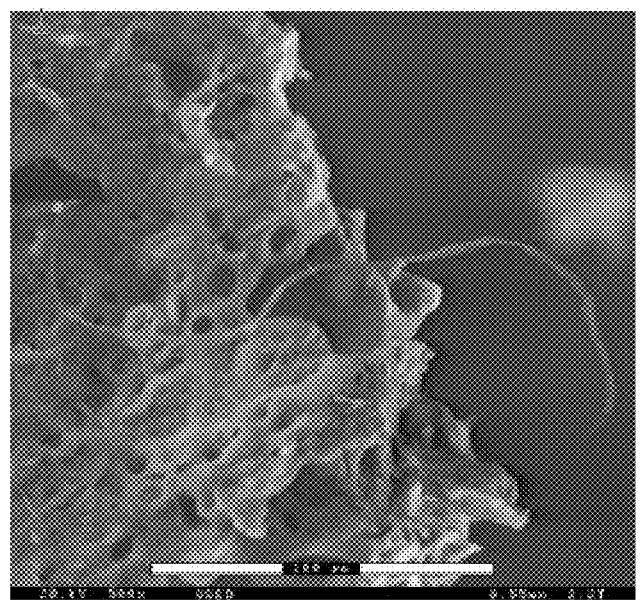
Figure 5:
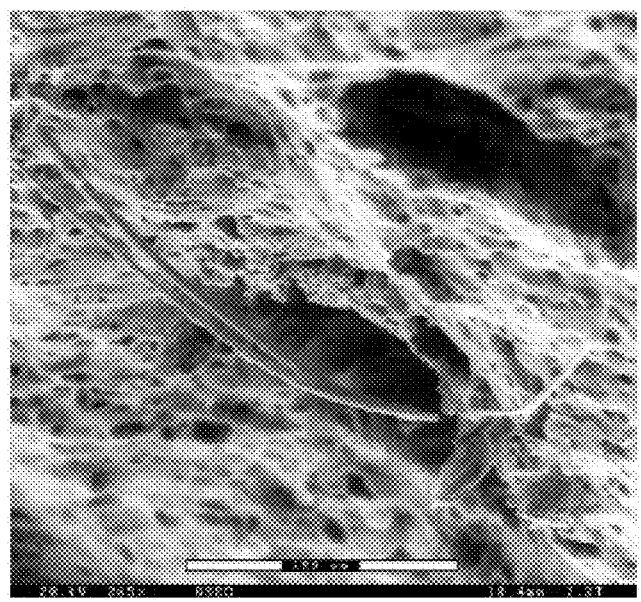
Figure 6:
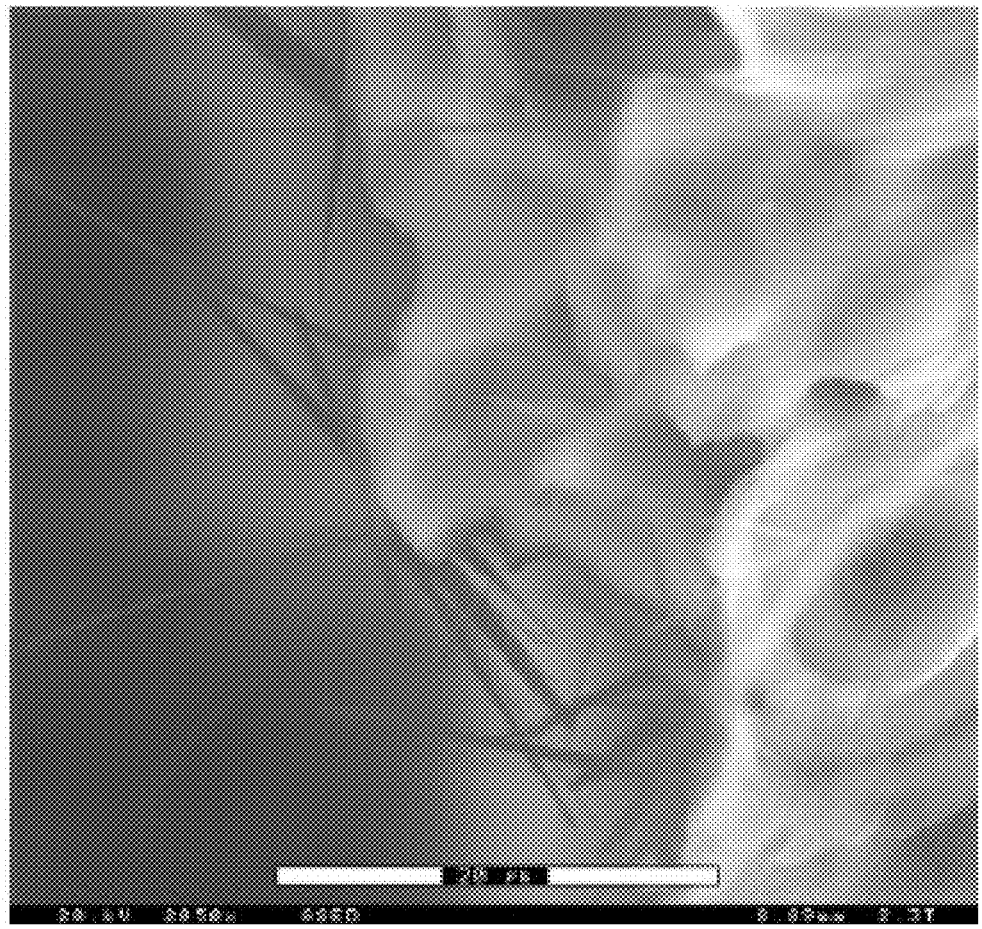

The present invention is based on the discovery that chiral zeolites may be prepared and employed as a packing material in liquid chromatographic separation of components in a mixture. The packing material, which acts as the stationary phase in liquid column chromatography, allows for the separation of a variety of types of components, including enantiomers.

I. CHROMATOGRAPHY

Chromatography generally comprises all separation techniques in which analytes partition between different phases that move relative to each other or exhibit different velocities. In most chromatography techniques, one phase is stationary while the other is mobile. As discussed above, in liquid chromatography, the mobile phase is a liquid and the stationary phase is either an immobilized liquid or a solid. High performance liquid chromatography (HPLC) includes all techniques which require elevated pressures to force the liquid through a packed bed of a stationary phase.

Traditional HPLC employs a polar adsorbent, such as silica or alumina, and a non-polar mobile phase, such as chloroform or petroleum ether. This type is known as normal phase chromatography, and it involves the interaction of polar analytes with polar sites on the surface of the packing. However, the technique has lost favor in view of the development of reversed-phase chromatography with a few exceptions.

In reversed-phase chromatography, a non-polar stationary phase is used in conjunction with a highly aqueous and polar mobile phase. About 80% of all HPLC applications employ reversed-phase chromatography (Neue, 1997). Some applications, such as protein separation, require a less hydrophobic-reversed phase. Proteins can easily be denatured by both polar and organic mobile phases. The hydrophobicity of the stationary phase may also need to be less so that the mobile phase used can be water or a diluted buffer. The technique employed in this case is called hydrophobic interaction chromatography. The analytes are adsorbed onto the packing in a buffer with a high salt concentration, and eluted with a buffer of low ionic strength.

Chiral chromatography is another type of liquid chromatography. One type of chiral chromatography relies upon modification of silica with an organic compound (typically chiral) such that the organic compound preferentially interacts with a particular enantiomer in a liquid racemic mixture. This type thus uses a "bonded" chiral stationary phase (CSP). Care must be taken when employing bonded CSP so as not to disrupt the bond between the organic compound and the silica.

II. CHROMATOGRAPHY COLUMNS

A. Silica

Most HPLC column packing materials are silica-based, and other types of chromatography also employ silica. The advantages of silica are its strength at high pressures, and its size stability upon exposure to different solvents. It does not swell or shrink in different solvents. However, the disadvantage of using silica in HPLC is the dissolution of silica at alkaline pH. The composition of the liquid mobile phase, the temperature and the chemistry of the surface bed affects the rate of the dissolution of silica. But, there are conditions, such as low temperature and use of various solvent modifiers, which can be maintained so that the silica beddings can withstand pHs up to, for example, 9.0 for a sustained period of time (Ahuja, 1991).

The surface of silica is composed of silanols and siloxane bridges or vicinal silanols:

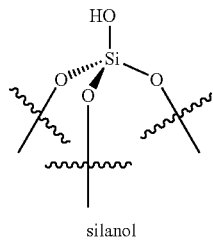

silanol

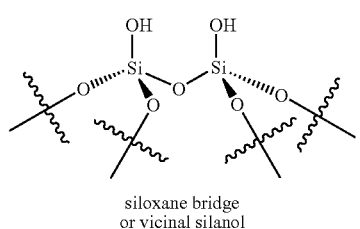

siloxane bridge
or vicinal silanol

The surface of fully hydroxylated silica, without metal impurities, has a pH of around 3. Thus, silanols are considered to be acidic. The adsorption centers are silanols in normal phase chromatography. Silanols are very hydrophilic and reactive towards the polar components of an analyte and a solvent. In surface modification of silica, silanols are the focus of interest. Siloxane bridges are very hydrophobic and unreactive (Ahuja, 1997).

B. Zeolites

Zeolites are crystalline microporous aluminosilicates with interconnected three-dimensional ordered cavities or pores. One can prepare zeolites from silica or modified silica. Within the cavities can lie cations, such as ammonium species, which balance the negative charges of aluminum (Li et al., 1999). Molecules of specific sizes and three-dimensional orientations can enter the pores (Arslan et al., 2006). Smaller or larger ones are not allowed and pass through. This unique property of zeolites may allow separation of mixtures that is not possible by other means (Arslan et al., 2006).

Alkali metal cations assist in the nucleation and crystal growth of zeolites by affecting the polymerization of the sodium silicate in the reacting gel. Sodium and potassium are non-limiting examples of such cations that may be used for this purpose (Yamanoto et al., 2003). Employing cations promotes the formation of crystalline layered zeolites as opposed to amorphous silica, which does facilitate compound separation (Yamanoto et al., 2003).

The size of the surface directing agent (SDA) can affect the crystalline structure and pore size of the zeolite (Wang et al., 2001). Larger chain hydrocarbons, for example, result in a wider pores (Rhodes et al., 2000).

As described by the present invention, chiral zeolites are aluminosilicates which have chiral pores. If a chiral zeolite is packed into a liquid chromatography column and subjected to a liquid comprising, for example, a pair of enantiomers, one of the enantiomers may enter the column and be retained longer, allowing the other enantiomer to pass through and elute first. Use of such zeolites may assist in separating enantiomers that may not be separable other chromatography methods. Other components of liquids may be separated using the chiral zeolites of the present invention as well.

To prepare chiral zeolites for use in liquid chromatography, chiral organic compounds are incorporated into zeolite silica during the synthesis of silica gel, followed by calcination for several hours (Lee, 2000; Swamy and Raghavendra, 2002; Nalwa, 2001). As a result, the chiral organic compounds are degraded or evaporated, leaving behind chiral pores in the material, called a packing material or a chiral stationary phase (CSP) (Huang et al., 2000; Wang et al., 2000; Lee et al., 2001). In this regard, the chiral organic compound may be considered a structure direction agent, or SDA. The CSP is then packed into a column. As discussed herein, generation of chiral zeolites takes place in few steps, resulting in an inexpensive and rapid manufacturing method. Variation in the molar ratio of substrates that allows for optimization of the chiral zeolites can be performed efficiently due to the simplicity of the preparation procedures (Zones et al., 2005).

Zeolites, such as chiral zeolites, may be characterized using a variety of methods, including electron diffraction spectroscopy (EDS) and scanning electron microscopy (SEM). EDS permits a structural analysis of the zeolites and SEM allows for the analysis of the morphology and the surface distribution of the silica-based stationary phase.

Without being bound by theory, the inventors believe that the proximity of the hydroxyl hydrogen in the cis- and trans-2-(N-methyl-N-phenylamino)cyclohexanols described herein is shared with the nearby amino nitrogen such that a partial charge is imparted onto the nitrogen group. This partial cationic charge may assist in the formation of crystalline silica. It should be noted that other chiral organic compounds may be designed to exploit such a feature in the formation of crystalline silica for chiral zeolites. Moreover, if a chiral organic compound does not possess such a feature, external alkali metal salts may be added to promote the formation of crystalline silica for chiral zeolites.

III. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents discussed in the Examples below are commercially available from known suppliers, such as Sigma-Aldrich.

Example 1

Synthesis of γ-Aminopropyl Silica Gel

The synthesis of γ-aminopropyl silica gel was carried out by reacting aminopropyl triethoxysilane (APTS) with commercial 5 μm particle size silica ($SiO_2$) gel (Lee, 2000). γ-Aminopropyl silica gel was then used in Example 4.

Example 2

Synthesis of Racemic trans-2-(N-methyl-N-phenylamino)cyclohexanol (MPAC)

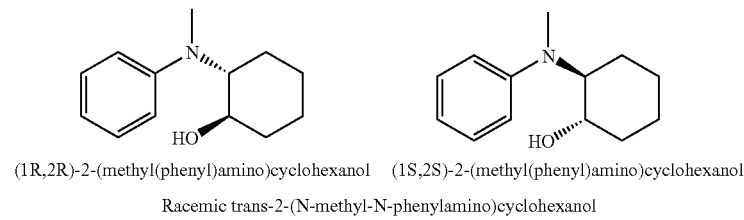

(1R,2R)-2-(methyl(phenyl)amino)cyclohexanol    (1S,2S)-2-(methyl(phenyl)amino)cyclohexanol Racemic trans-2-(N-methyl-N-phenylamino)cyclohexanol To a 500 mL round bottom flask was added 100 mL of 1.2 M potassium t-amylate in cyclohexane (0.12 moles) and 41.7 mL of cumene (0.3 moles) under a constant flow of nitrogen gas. Then 10.8 mL of N-methylaniline (0.1 moles) was added to the reaction mixture while the reaction was continuously stirred. n-Butyllithium (46 mL of a 2.2 M solution, 0.1 moles) was added and the resulting amide was left stirring for two days. Cyclohexene oxide (10.1 mL, 0.1 moles) was added. After 24 hours, the reaction was quenched by carefully adding water under the flow of nitrogen. Washing of the product with 100 mL of distilled water yielded two layers of which the organic layer was extracted. Repeated rotovapor distillations removed most of the cumene. Any leftover cumene after rotovapor distillation was removed by vacuum horizontal distillation. This device employs a vacuum (<1 mm Hg) and liquid nitrogen to trap cumene, which distilled at about 85° C., but 16 g of racemic MPAC (0.075 moles, 75% yield) distilled at 120° C. The product, MPAC, was analyzed by NMR spectroscopy and the spectrum confirmed the presence of the compound when it was compared to that of literature (Swamy and Raghavendra, 2002).

When the presence of a few extra peaks in the NMR indicated that there may be a small amount of trans-2-(1-methyl-1-phenylethyl)cyclohexanol (TCC) in the product, the product was exposed to the flow of hydrogen chloride gas for one hour in order to protonate the product, MPAC. TCC was not protonated and was separated. The MPAC salt was placed inside the refrigerator over night and the product solidified. The portion of materials in the flask that did not solidify and stayed in the liquid form is most likely the contaminant, TCC. The solid material was the compound of interest and the contamination was decanted or drained off. To recover the sample, it was washed with concentrated potassium hydroxide solution three times and the free amine was vacuum distilled two times to remove solvent. The sample was analyzed by NMR spectroscopy and the presence and purity of the final product, trans-2-(N-methyl-N-phenylamino)cyclohexanol, was confirmed (Swamy and Raghavendra, 2002).

Example 3

Resolution of MPAC Enantiomers

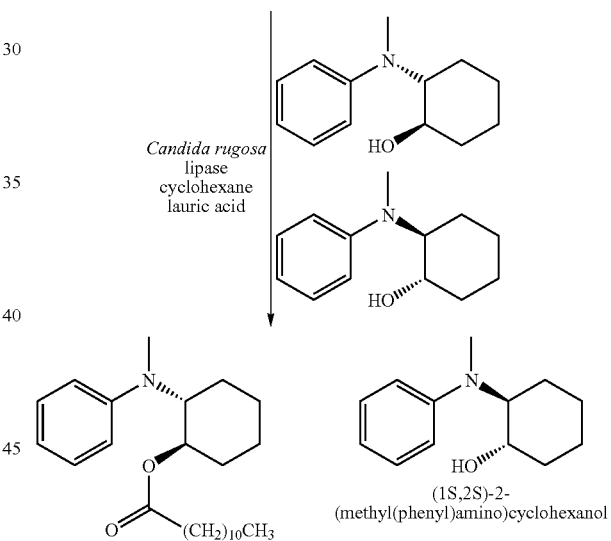

Resolution of enantiomers of racemic MPAC from Example 2 was accomplished using *Candida rugosa* lipase, which is a natural biological enzyme. For every 10 mmoles or 2.11 g of MPAC, 6.6 g of lipase, 40 mL of cyclohexane, and 10 mmoles or 2 g of lauric acid were used. The reaction was left at 38° C. for 48 hours after which esterification was tested using chiral HPLC (Chiralcel® OJ; 5% isopropanol and 95% hexanes; 1 mL per minute). Formation of ester was confirmed by HPLC (FIG. 1), and the reaction stopped. Rotovapor distillation followed by radial chromatography separated the ester from that of un-reacted (1S, 2S)-aminoalcohol ("the 1S,2S MPAC enantiomer").

During esterification, should be taken not to exceed a reaction time of 48 hours since the other enantiomer will start esterifying as well. HPLC testing for esterification should be performed to follow the esterification reaction (e.g., once every 6-24 hours). Moreover, well-known methods may be employed to remove the ester group from the esterified product to generate the 1R,2R amino alcohol. See March's Advanced Organic Chemistry, 2007, incorporated herein by reference. This enantiomer may alternatively be used to prepare chiral zeolites and columns comprising such zeolites using the methods taught herein.

Example 4

Preparation of A Chiral Zeolite Column Using the 1S,2S MPAC Enantiomer

The synthesis of chiral zeolites begin with mixing aminopropyltriethoxysilane (APTS), the 1S,2S MPAC enantiomer and sodium silicate in a 1:1:1 molar ratio. Next, aluminum hydroxide was added in a 0.3:1.0 molar ratio compared to that of silica. The mixture was refluxed for 36 hours. After reflux, the sample was washed 3 times with 10 mL of methanol and 10 mL of pentane. The white powder was then placed in an oven and calcinated for 8 hours at 550° C. After 8 hours, the oven was turned off and slow cooling inside the oven allowed the sample to reach room temperature within a few hours. The sample was taken out of the oven for grinding and it was converted into a fine powder for packing into a column.

The powdered gray material exhibited particle sizes of less than 1 mm in diameter. The material (3.2 g) was packed into a 25 cm×4.6 mm stainless steel HPLC column and mechanically compressed to further the packing. To improve the packing, direct pressure was applied on the inner boar of the column with a press and 0.5 g more material was added to completely fill the column.

The packed HPLC column was connected between an HPLC pump (Spectra Physics, P1500) and detector (Spectra Physics, UV 2000). Prior to running any samples on the column, an overnight run of isopropyl alcohol (1 mL/min.) washed any possible impurities and provided a stable base line for the detector. The flow rate of 1 mL/min. causes a pressure of about 1000 psi, which further compressed the materials.

Example 5

Resolution of Racemic trans-2-(1-Methyl-1-phenylethyl)cyclohexanol (TCC)

Figure 7:
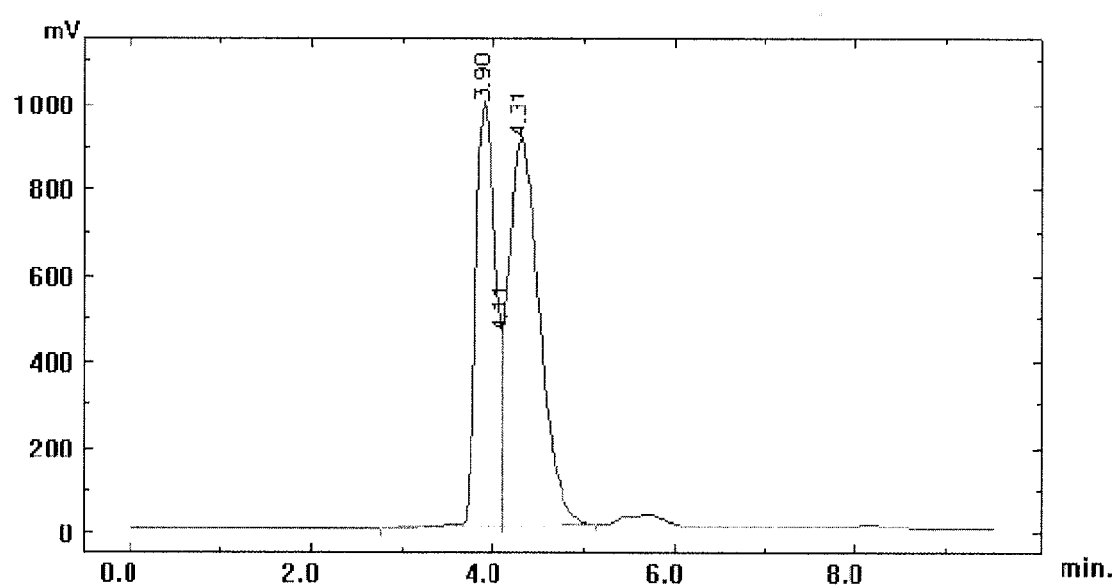
FIG. 7. HPLC chromatogram of resolution of trans-2-(1-methyl-1-phenylethyl)cyclohexanol (TCC) using a chiral 1S,2S MPAC enantiomer zeolite column. 85% isopropanol, 15% hexanes; 0.5 mL/min.

Racemic trans-2-(1-methyl-1-phenylethyl)cyclohexanol (TCC) was resolved using the chiral zeolite column of Example 4 (85% isopropanol, 15% hexanes; 0.5 mL/min.). A chromatogram is shown in FIG. 7.

Example 6

Calcination Temperature Studies

A series of reactions were performed in order to optimize the temperature for the calcination described in Example 4. Temperatures were varied from 350, 400, 450, 500, 550, 575, 600 and 650° C. Analysis of the chiral zeolites after each experiment was performed using Scanning Electron Microscopy (SEM).

Below 500° C., the SEM images show little or no evidence of pores forming in the material. Above 550° C., the SEM images show evidence of melting by formation of long tube-like crystals extending into the bulk of the silica with interconnected channels. The gross morphology upon removal of the material calcined at 550° C. from the furnace is gray and spongy. SEM images at different temperatures are shown in FIGS. 2-6.

Example 7

Sodium Silicate:1S,2S MPAC Enantiomer Molar Ratio Study

Figure 8:
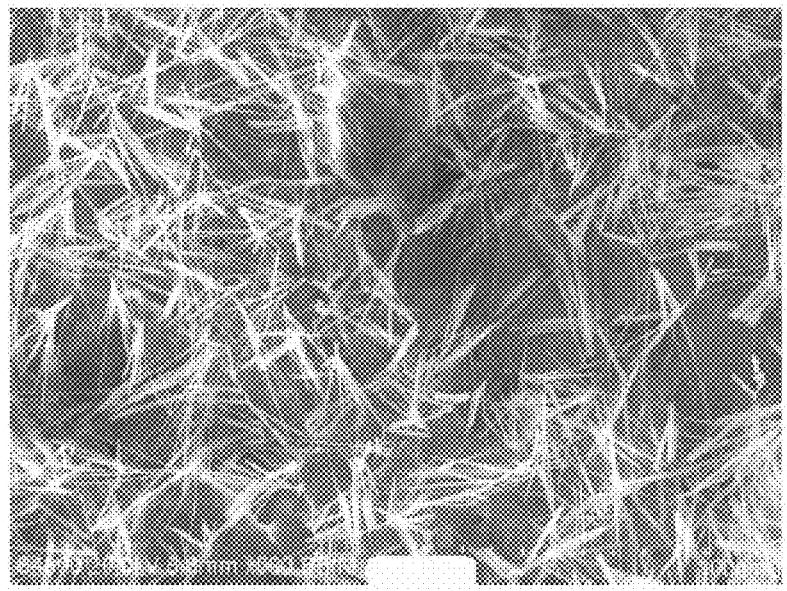
FIG. 8. Scanning electron micrographs of chiral zeolites at varying sodium silicate: 1S,2S MPAC enantiomer ratios.
Figure 8:

The ratio of sodium silicate to the 1S,2S MPAC enantiomer was varied from the initial 1:1 mole ratio used in the Examples above. With a calcination temperature of 550° C., the sodium silicate:1S,2S MPAC enantiomer ratio was prepared at 1:0.25 and 1:2. Following analysis by SEM and HPLC resolution of TCC as described in Example 5, it was determined that the 1:1 ratio was preferred: neither of the other ratios produced a material that was as porous as the material prepared at a 1:1 ratio. SEM images are shown in FIG. 8.

All of the methods disclosed and claimed can be made and executed without undue experimentation in light of the present disclosure. While the methods of this invention have been described in terms of embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope, and concept of the disclosure as defined by the appended claims.

REFERENCES

The following references, to the extent that they provide exemplary procedural or other details supplementary to those set forth herein, are specifically incorporated herein by reference.

Ahuja, S., *Chiral Separation By Liquid Chromatography*, ACS Symposium, Washington, D.C., vol. 471, Chapter 1, 1991.
Arlsan et al., *Turk. J. Chem.,* 30:203-210, 2006.
Huang et al., *J. Amer. Chem. Soc.,* 122:3530, 2000.
Lee, W. Y., *Environmental Applications of Chiral HPLC and Development of New Chiral Stationary Phases*, Wiley & Sons, New York, 2000, pp 1-10.
Lee et al., *J. Amer. Chem. Soc.,* 123:9769, 2001.
Li et al., *Nature,* 402:276, 1999.
March's Advanced Organic Chemistry: Reactions, Mechanisms, and Structure (March's Advanced Organic Chemistry), Smith and March (Eds.), 2007.
Nalwa, H. (Ed.), *Silicon Based Materials and Devices, Vol. 2: Properties and Devices*, Academic Press, San Diego, 2001.
Neue, D. U., *HPLC Columns: Theory, Technology, and Practice*, Wiley & Sons, New York, 1997, pp 1-100.
Peterson, P. V, *J. Chromotography A,* 757:65-71, 1997.
Refaei, M. N., "Synthesis and Characterization of trans-2-(N-Methyl-N-phenylamino)cyclohexanol For the Fabrication of A Novel High Performance Liquid Chromatography Column," Masters Thesis, Materials Research Institute, University of Texas at El Paso, 2007, pp 1-65.
Rhodes et al., *Chem. Mater.,* 12:2832, 2000.
Stinson, C. S., *CENEAR,* 78:55-78, 2007.
Subramanian, G., *A Practical Approach To Chiral Separation*, VCH Publisher, New York, 1994, pp 11-94.
Swamy and Raghavendra, *Syn. Comm.,* 2002, CAN 138: 122422 AN 2002: 612857.

Wang et al., *Langmiur*, 17:2572, 2001.
Wang et al., *Chem. Commun.*, p 2333, 2000.
Yamanoto et al., *Science*, 300:470, 2003.
Zones et al., *J. Phys. Chem. B*, 109:661, 2005.

What is claimed is:

1. A method of making a packing material for liquid chromatography comprising:
   (a) forming a first mixture by combining sodium silicate and a compound of formula (I)

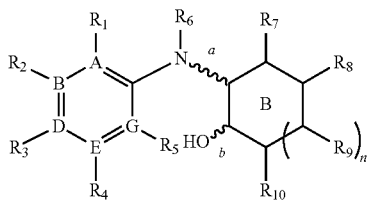

wherein:
A, B, D, E and G are each independently carbon or nitrogen;
$R_1$-$R_5$ are each independently absent, hydrogen, or alkyl$_{(C\leq4)}$, wherein if any of A, B, D, E, or G is nitrogen, then $R_1$-$R_5$ is absent;
$R_6$ is alkyl$_{(C\leq4)}$;
$R_7$-$R_{10}$ are each independently hydrogen, or alkyl$_{(C\leq4)}$;
the bonds marked "a" and "b" are cis or trans to one another; and
n=0 or 1, such that when n=0, then the ring marked as "B" is a five-membered ring, and when n=1, the ring marked as "B" is a six-membered ring;

(b) adding $Al^{3+}$ to the first mixture to form a second mixture;
   (c) refluxing the second mixture; and
   (d) calcinating the second mixture to form the packing material.

2. The method of claim 1, further comprising packing a liquid chromatography column with the packing material.

3. The method of claim 1, further comprising adding aminopropyltriethoxysilane (APTS) to either the first or second mixture before refluxing.

4. The method of claim 3, wherein the molar ratio of aminopropyltriethoxysilane to the compound of formula (I) is about 1:1.

5. The method of claim 1, further comprising washing the second mixture with at least one organic solvent.

6. The method of claim 5, wherein the organic solvent is a polar solvent.

7. The method of claim 5, wherein the organic solvent is a non-polar solvent.

8. The method of claim 1, wherein the molar ratio of sodium silicate to the compound of formula (I) is about 1:1.

9. The method of claim 1, wherein the molar ratio of $Al^{3+}$ to total silica ranges from about 0.1:1 to 1:1.

10. The method of claim 9, wherein the molar ratio of $Al^{3+}$ to total silica ranges from ranges from about 0.3:1.

11. The method of claim 1, wherein calcination is performed at a temperature ranging from about 525-575° C.

12. The method of claim 1, wherein the compound of formula (I) is further defined as trans-2-(N-methyl-N-phenylamino)cyclohexanol.

13. The method of claim 12, wherein trans-2-(N-methyl-N-phenylamino)cyclohexanol is further defined as 1S,2S-2-(N-methyl-N-phenylamino)cyclohexanol.

* * * * *